United States Patent
Nakano et al.

[11] Patent Number: 6,052,428
[45] Date of Patent: Apr. 18, 2000

[54] MEDICAL RADIOGRAPHIC APPARATUS AND PATIENT'S HEAD FIXING DEVICE

[75] Inventors: Kozo Nakano; Minoru Watanabe; Masanori Otsuka; Kazuyuki Fujita, all of Kyoto, Japan

[73] Assignee: J. Morita Manufacturing Corporation, Kyoto, Japan

[21] Appl. No.: 08/848,304

[22] Filed: Apr. 30, 1997

Related U.S. Application Data

[63] Continuation of application No. 08/410,229, Mar. 24, 1995, Pat. No. 5,642,392.

[30] Foreign Application Priority Data

Apr. 12, 1994 [JP] Japan ........................... 6-73606
Apr. 13, 1994 [JP] Japan ........................... 6-75195

[51] Int. Cl.[7] ........................................ A61B 6/14
[52] U.S. Cl. ............................... 378/38; 378/197
[58] Field of Search .................. 378/38–40, 197

[56] References Cited

U.S. PATENT DOCUMENTS 3,737,660  6/1973  Ando ........................... 378/39

FOREIGN PATENT DOCUMENTS

3530234 A1  2/1987  Germany.
3703050 A1  8/1987  Germany.

Primary Examiner—Craig E. Church
Attorney, Agent, or Firm—Koda & Androlia

[57] ABSTRACT

The invention provides a medical radiographic apparatus constituted such that a swivel arm possessing an X-ray generator and an X-ray detection plane disposed to confront mutually with respect to the head of a patient is supported with a post through swivel means and a holding frame thereof in order to move the swivel arm about the head of the patient, the X-ray generator and X-ray detection plane are moved in mutually parallel reverse directions while synchronized, and irradiated X-rays are allowed to always enter the X-ray detection plane by passing through the same exposure region in the desired plane section in cooperation with the movement, the apparatus comprising:

an ascending/descending main body from which the holding frame is extended, supported with the post so as to be free to move up and down, and a patient frame supported with the post so as to be free to move up and down, independently of the ascending/descending main body, having holding means for holding and fixing the head of the patient.

1 Claim, 16 Drawing Sheets

MEDICAL RADIOGRAPHIC APPARATUS AND PATIENT'S HEAD FIXING DEVICE

This application is a continuation of application Ser. No. 08/410,229, filed Mar. 24, 1995, now U.S. Pat. No. 5,642,392.

BACKGROUND OF THE INVENTION

1. Field of the Invention

The present invention relates to a medical radiographic apparatus capable of performing plane tomography or both plane tomography and curvature tomography, preferably used in dentistry or otorhinolaryngology, and the patient's head fixing device used in the medical radiographic apparatus.

2. Description of the Related Art

FIG. 15 is a side view showing the constitution of a conventional radiographic apparatus 100 commonly used for plane tomography and curvature tomography used in dentistry or otorhinolaryngology. This radiographic apparatus generally comprises a swivel arm 101, a lift main body 102, a patient frame 103, a post 104, and a base 105.

The swivel arm 101, which is formed roughly in a U-form, comprises an X-ray generator and a slit plate, which are attached to one end 101a thereof, a film cassette and a slit plate, which attached to the other end 101b thereof, and includes a built-in X-ray detecting means realized by a displacement drive mechanism of the film cassette or charge coupled device (CCD).

The area in the middle 101c of the swivel arm 101 is suspended from a holding frame 108 through swivel means 107, and this holding frame 108 is extended integrally from the ascending/descending main body 102. The swivel means 107 incorporates a swivel mechanism table for swiveling the swivel arm 101, and an XY table. Therefore, it is possible to swivel the swivel means 107 along the shape of the dental arch of the patient, so that a radiograph of the entire mouth can be taken, that is, panoramic radiography or curvature tomography may be realized.

Moreover, as explained specifically in the Japanese Patent Applications 4-13988 and 5-307170 previously filed by the present applicant, by moving the X-ray generator and X-ray detection plane in mutually parallel reverse directions while synchronized, and passing the irradiation X-rays constantly along the same region of the desired plane section by cooperating with the movement, a plane tomograph can be taken at an arbitrary section of the teeth, dentition, and mandibular joint.

The ascending/descending main body 102 is designed to move up and down in the vertical direction along a guide groove 106 on the post 104, by unlocking and manipulating an electromagnetic brake (not shown) or a lock handle 109, and when the electromagnetic brake is applied or when the lock handle 109 is locked, the ascending/descending main body 102 is fixed and supported on the post 104. The post 104 is planted on the base 105.

A handle 118 is provided at the lower side of the patient frame 103, and with the patient gripping this handle 118, the position of the patient 112 in radiography can be stabilized, while the shoulders of the patient 112 are lowered so as not to interfere with the movement of the swivel arm 101.

A header holder 114 for positioning and holding the head 113 of the patient 112 comprises a frontal holding member 115 abutting against the forehead of the head 113 of the patient 112, a pair of temporal holding members 116 abutting against the both temporal regions of the patient 112, and a chin rest 117a for resting the jaw of the patient 112. The head holding members 115, 116 are installed downward from the middle 101c of the swivel arm 101. The chin rest 117a is fixed to the patient frame 103 through a chin rest support member 117. Being fixed to the patient frame 103 or ascending/descending main body 102, it is free to move up and down together with the ascending/descending main body 102.

In a thus constituted radiographic apparatus 100, the radiologist adjusts the ascending/descending main body 102 by ascending or descending according to the height of the patient 112, displaces the chin rest 117a in the longitudinal direction of the patient 112, while expanding or contracting, and adjusts the exposure position of the head 113 to coincide with the X-ray irradiation plane, and then takes a radiograph.

In panoramic radiography, generally, an oblong film of 150×300 mm is used in almost the entire area, but in plane tomography, the irradiation field is about 70×80 mm, so that plural plane tomographs can be taken on one film for a panorama.

In dental treatment or orthodontic therapy, hitherto, so-called panoramic radiographing of the entire dental arch by using X-rays or tomography from an arbitrary direction near a target tooth has been utilized. In such a method, especially when observing the process, it is extremely important to assure its repeatability by always irradiating the site with the same dose of exposure. Furthermore, unless the head of the patient is fixed firmly, the formed image may deteriorate due to blurring or the like. Hence, the apparatus for fixing the head of the patient has been used.

FIG. 16 is a side view schematically showing a typical conventional head fixing device 301. This head fixing device 301 roughly comprises a pair of right and left temporal holding members 302, a chin rest 303, and guide means 304. First, while the pair of temporal holding members 302 are apart from each other, the patient places the head between the temporal holding members 302, and then the temporal holding members 302 come closer to each other, and protruding ear rods 305 provided at respective free ends 302a thereof are fitted into the external auditory meatus, so that the ears of the patient are positioned. Subsequently to this state, the main body 303b of the chin rest 303 is expanded or contracted in the direction of arrow 306 so that the lower jaw of the patient may be placed on a platform 303a of the chin rest 303, and is displaced in the direction of arrow 307 by guide means 304. In this way, the lower jaw of the patient is positioned, and while the oculoauricular horizontality is kept, that is, the line linking the external auditory meatus and the eye of the patient is horizontal, for example, the panoramic or tomographic picture is taken.

In the radiographic apparatus 100 applicable in both plane tomography and curvature tomography, however, it is difficult to take upper and lower remote positions correctly in the center of the irradiation field of the film, for example, when the mandibular joint is located in an upper position and the lower jaw end is located at a lower position.

Moreover, in the prior art in FIG. 16, in order to achieve the oculoauricular horizontality by varying the slant angle of the face of the patient, one must match the indication beam emitted from the ascending/descending main body or the like with the face of the patient, and then the expansion or contraction and displacement of the chin rest 303 must be repeated alternately, and thus controllability is poor. It is also the same in the construction for supporting the head of the patient from beneath the head as in the prior art shown in FIG. 16, or in the construction for fixing the head of the patient from above as being installed near the mounting part of the swivel arm.

SUMMARY OF THE INVENTION

It is hence a primary object of the invention to provide a medical radiographic apparatus capable of expanding the region to be radiographed and taking the radiograph of a desired area with high precision, and a patient's head fixing device capable of fixing the head of the patient in a desired position with excellent controllability.

The invention provides a medical radiographic apparatus constituted such that a swivel arm possessing an X-ray generator and an X-ray detection plane disposed to confront mutually with respect to the head of a patient is supported with a post through swivel means and a holding frame thereof in order to move the swivel arm about the head of the patient, the X-ray generator and X-ray detection plane are moved in mutually parallel reverse directions while synchronized, and irradiated X-rays are allowed to always enter the X-ray detection plane by passing through the same exposure region in the desired plane section in cooperation with the movement, the apparatus comprising:

an ascending/descending main body from which the holding frame is extended, supported with the post so as to be free to move up and down, and a patient frame supported with the post so as to be free to move up and down, independently of the ascending/descending main body, having holding means for holding and fixing the head of the patient.

The invention also provides a medical radiographic apparatus constituted such that a swivel arm possessing an X-ray generator and an X-ray detection plane disposed to confront mutually with respect to the head of a patient is supported with a post through swivel means and a holding frame thereof in order to move the swivel arm about the head of the patient, the X-ray generator and X-ray detection plane are moved in mutually parallel reverse directions while synchronized, and irradiated X-rays are allowed to always enter the X-ray detection plane by passing through the same exposure region in the desired plane section in cooperation with the movement, the apparatus comprising:

an ascending/descending main body from which the holding frame is extended, supported with the post so as to be free to move up and down, and a patient frame supported so as to be free to move up and down on the ascending/descending main body, having holding means for holding and fixing the head of the patient.

The invention further presents a medical radiographic apparatus constituted such that a swivel arm possessing an X-ray generator and an X-ray detection plane disposed to confront mutually with respect to the head of a patient is supported with a post through swivel means and a holding frame thereof in order to move the swivel arm about the head of the patient, the X-ray generator and X-ray detection plane are moved in mutually parallel reverse directions while synchronized, and irradiated X-rays are allowed to always enter the X-ray detection plane by passing through the same exposure region in the desired plane section in cooperation with the movement, the apparatus comprising:

a patient frame supported so as to be free to move up and down in relation to the post, having holding means for holding and fixing the head of the patient, and an ascending/descending main body from which the holding frame is extended, supported with the patient frame so as to be free to move up and down in relation to the patient frame.

The invention further provides a medical radiographic apparatus constituted such that a swivel arm possessing an X-ray generator and an X-ray detection plane disposed to confront mutually with respect to the head of a patient is supported with a post through swivel means and a holding frame thereof in order to move the swivel arm about the head of the patient, the X-ray generator and X-ray detection plane are moved in mutually parallel reverse directions while synchronized, and irradiated X-rays are allowed to always enter the X-ray detection plane by passing through the same exposure region in the desired plane section in cooperation with the movement, the apparatus comprising:

a patient frame supported so as to be free to move up and down in relation to the post, having holding means for holding and fixing the head of the patient, and an ascending/descending main body from which the holding frame is extended, supported with the patient frame so as to be free to move up and down.

The invention further provides a medical radiographic apparatus constituted such that a swivel arm possessing an X-ray generator and an X-ray detection plane disposed to confront mutually with respect to the head of a patient is supported with a post through swivel means and a holding frame thereof in order to move the swivel arm about the head of the patient, the X-ray generator and X-ray detection plane are moved in mutually parallel reverse directions while synchronized, and irradiated X-rays are allowed to always enter the X-ray detection plane by passing through the same exposure region in the desired plane section in cooperation with the movement, the apparatus comprising:

elevating/lowering means interposed between the swivel arm and the holding frame, for supporting the swivel means so as to be free to move up and down in relation to the holding frame, an ascending/descending main body from which the holding frame is extended, supported with the post so as to be free to move up and down, and a patient frame having holding means for holding and fixing the head of the patient, fixed on the ascending/descending main body.

The invention further provides a medical radiographic apparatus constituted such that a swivel arm possessing an X-ray generator and an X-ray detection plane disposed to confront mutually with respect to the head of a patient is supported with a post through swivel means and a holding frame thereof in order to move the swivel arm about the head of the patient, the X-ray generator and X-ray detection plane are moved in mutually parallel reverse directions while synchronized, and irradiated X-rays are allowed to always enter the X-ray detection plane by passing through the same exposure region in the desired plane section in cooperation with the movement, the apparatus comprising:

an ascending/descending main body from which the holding frame is extended, supported with the post so as to be free to move up and down, a patient frame having holding means for holding and fixing the head of the patient, fixed on the ascending/descending main body, and elevating/lowering means for supporting the X-ray generator so as to be free to move up and down in relation to the patient frame.

The invention is characterized in that the X-ray generator and X-ray detection plane swivel about the head of the patient while keeping a confronting relation therebetween to the head of the patient, and in cooperation with the swivel, the X-ray detection plane is moved in a direction nearly vertical to the X-ray irradiation direction from the X-ray generator, thereby taking a curvature tomograph of the maxillofacial section of the head.

Further, the invention is characterized in that the patient frame or ascending/descending main body is provided with a plane section indication light beam generator.

Further, the invention is characterized in that the ascending/descending main body is provided with a median line indication light beam generator and an oculoauricular horizontal line light beam generator and the swivel arm is provided with a curvature section position indication light beam generator.

Further, the invention is characterized in that input means for setting radiographic conditions is provided on the top of the patient frame.

Still further, the invention is characterized in that display means for displaying an exposure position and radiographic conditions corresponding to the input operation of the radiographic conditions is provided adjacently to the input means.

The invention provides a patient's head fixing device comprising:

a pair of temporal holding members provided so as to be free to move closer to and remote from both temporal regions of the patient, protrusions to be fitted into the external acoustic meatus of the patient, provided at respective free ends of the temporal holding members, a telescopic support member for supporting the patient with the free end thereof by abutting against the jaw or subnasal point of the patient, and guide means for guiding the base end of the support member so that the distance from the base end to the protrusion may be constant.

The support member of the invention comprises:

a guide pin for guiding the support member on the guide means so as to be free to run, a brake means disposed oppositely to the guide means, a release button to be operated by pushing, a link mechanism for linking the release button and brake means, and a spring member for pressing the brake means to the guide means.

The invention is characterized in that at least the temporal holding members and protrusions are made of X-ray permeable materials.

According to the invention, the radiographic apparatus is constituted such that a swivel arm possessing an X-ray generator and an X-ray detection plane (e.g. X-ray film, X-ray detection element) disposed to confront mutually with respect to the head of a patient is held on a holding frame through swivel means provided with a swivel motor and an X-Y table, thereby it is made possible to swivel the swivel arm about the head of the patient in a desired locus and irradiate a desired exposure site with X-ray, the X-ray generator and X-ray detection plane are moved in mutually parallel reverse directions while synchronized, and irradiated X-rays are allowed to always enter the X-ray detection plane by passing through the same exposure region in the desired plane section in cooperation with the movement.

Therefore, the image in the same exposure site is detected on the X-ray detection plane, while images in the regions remote from the exposure site are blurry and displayed as noise components, so that the tomogram of the exposure site in the desired plane section is obtained.

According to the invention, in a thus constituted radiographic apparatus, the holding frame is extended from the ascending/descending main body supported with the post so as to be free to move up and down, and the patient frame having holding means for holding and fixing the head of the patient, is supported with the post so as to be free to move up and down, independently of the ascending/descending main body.

Further, according to the invention, the ascending/descending main body from which the holding frame is extended is supported with the post so as to be free to move up and down, and the ascending/descending main body supports the patient frame so that the patient frame is free to move up and down on the ascending/descending main body.

Further, according to the invention, the patient frame is supported with the post so as to be free to move up and down, and the ascending/descending main body from which the holding frame is extended is supported so as to be free to move up and down in relation to the patient frame.

According to the invention, the patient frame is supported with the post so as to be free to move up and down, and the ascending/descending main body from which the holding frame is extended is supported with the patient frame so as to be free to move up and down.

Further, according to the invention, elevating/lowering means for supporting the swivel means so as to be free to move up and down in relation to the holding frame is interposed between the swivel arm and the holding frame, and the ascending/descending main body from which the holding frame is extended and to which the patient frame is fixed is supported with the post so as to be free to move up and down.

Further, according to the invention, the ascending/descending main body from which the holding frame is extended and to which the patient frame is fixed is supported with the post so as to be free to move up and down, and the X-ray generator is supported so as to be free to move up and down in relation to the patient frame by the lift means.

Thus, according to the invention, at least the X-ray generator and patient frame are possible to move up and down relative to each other, so that radiographing of a desired site may be carried out with high precision as well as the exposure region to be radiographed extended.

More preferably, the X-ray generator and X-ray detection plane swivel about the head while keeping a confronting relation to the head of the patient, and the X-ray detection plane is moved, in cooperation with the swivel, in a direction nearly vertical to the irradiation direction of X-ray from the X-ray generator, thereby allowing a curvature tomography of the maxillofacial section of the head to be taken. As a result, both plane tomography achieved by displacement of the X-ray generator and X-ray detection plane in mutually parallel reverse directions, and curvature tomography such as panoramic radiography may be realized.

Yet preferably, the patient frame or ascending/descending main body is provided with a plane section indication light beam generator, whereby more accurate positioning is possible in the plane tomography mentioned above.

Still more preferably, the ascending/descending main body is provided with a median line indication light beam generator and an oculoauricular horizontal line indication light beam generator, while the swivel arm is provided with a curvature section tomographic position indication light beam generator. Thereby, the patient can be positioned accurately in performance of the curvature tomography mentioned above.

Further preferably, input means such as a switch panel for setting radiographic conditions may be provided on the top of the patient frame, and more preferably, adjacently thereto, display means such as a liquid crystal panel for displaying the exposure position and radiographic conditions corresponding to the input operation of the radiographic conditions may be provided. The patient frame is furnished with holding means for holding and fixing the head of the patient, and therefore the operator can register the radiographic conditions in the same position as when positioning the patient, so that controllability may be enhanced.

Also according to the invention, the head of the patient is placed between the temporal holding members in a mutually apart state, and then the temporal holding members are brought closer to each other to pinch the temporal sides of the patient. At this time, the protrusions provided at the free ends of the temporal holding members are fitted into the external acoustic meatus of the patient. The protrusions are thus positioned on the basis of the external acoustic meatus. Furthermore, the holding member is expanded or contracted to be positioned so that the free end of the holding member may abut against the jaw or subnasal point of the patient. In succession, the base end of the support member is guided and displaced by the guide means.

The guide means has an arc locus so that the distance from the base end of the support member to the protrusion may be always constant, and therefore even if, for example, the tilt angle of the head of the patient is adjusted so as to keep the eye-ear plane of the patient horizontal, since the distance from the base end of the support member to the protrusion is constant, it is not necessary to adjust the expansion of the support member, and only the support member is displaced on the guide means, so that the head of the patient may be fixed in a desired position with such excellent controllability.

More preferably, the support member has a guide pin provided at its base end so as to travel on the guide means, and the base end is provided with brake means confronting the guide means. In response to this, the brake means is coupled to the release button through a link mechanism, and the brake means is thrust by a spring member to contact with the guide means with pressure. Therefore, the operator has only to press the release button to separate the brake means from the guide means by resisting the elastic force of the spring member, and release the release button when the tilt angle of the face of the patient comes to the desired tilt angle, thereby positioning the patient in a desired position.

Further preferably, at least the temporal holding members and protrusions are made of materials high in X-ray permeability and rigidity, such as acrylic resin, carbon fiber reinforced plastics, and polycarbonate, so that these members can be prevented from being included in radiographic images.

BRIEF DESCRIPTION OF THE DRAWINGS

Other and further objects, features, and advantages of the invention will be more explicit from the following detailed description taken with reference to the drawings where.

DETAILED DESCRIPTION OF THE PREFERRED EMBODIMENTS

Figure 1:
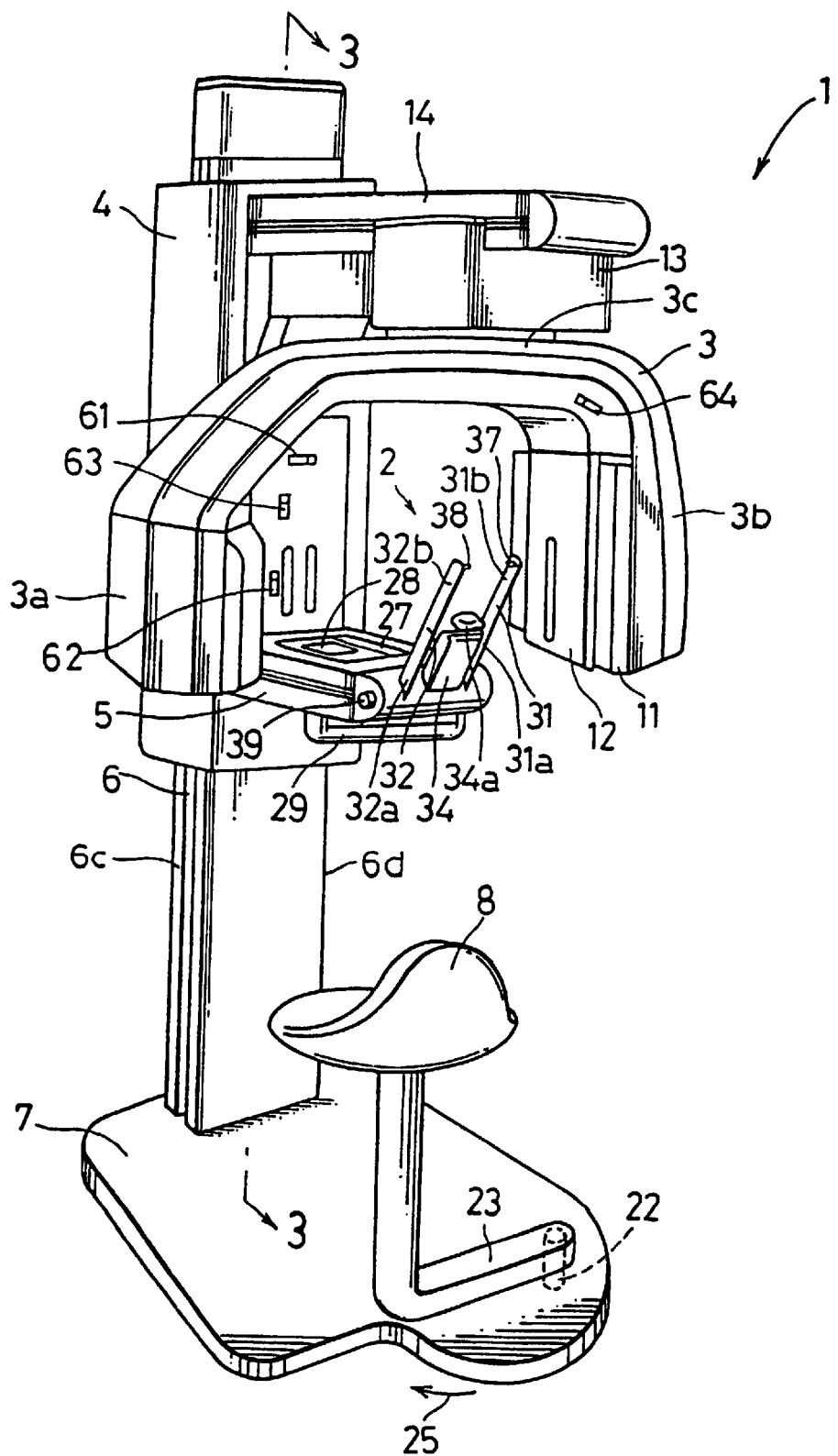
FIG. 1 is a perspective view of a radiographic apparatus 1 in a first embodiment of the invention.

Now referring to the drawings, the preferred embodiments of the invention are described below.

Figure 2:
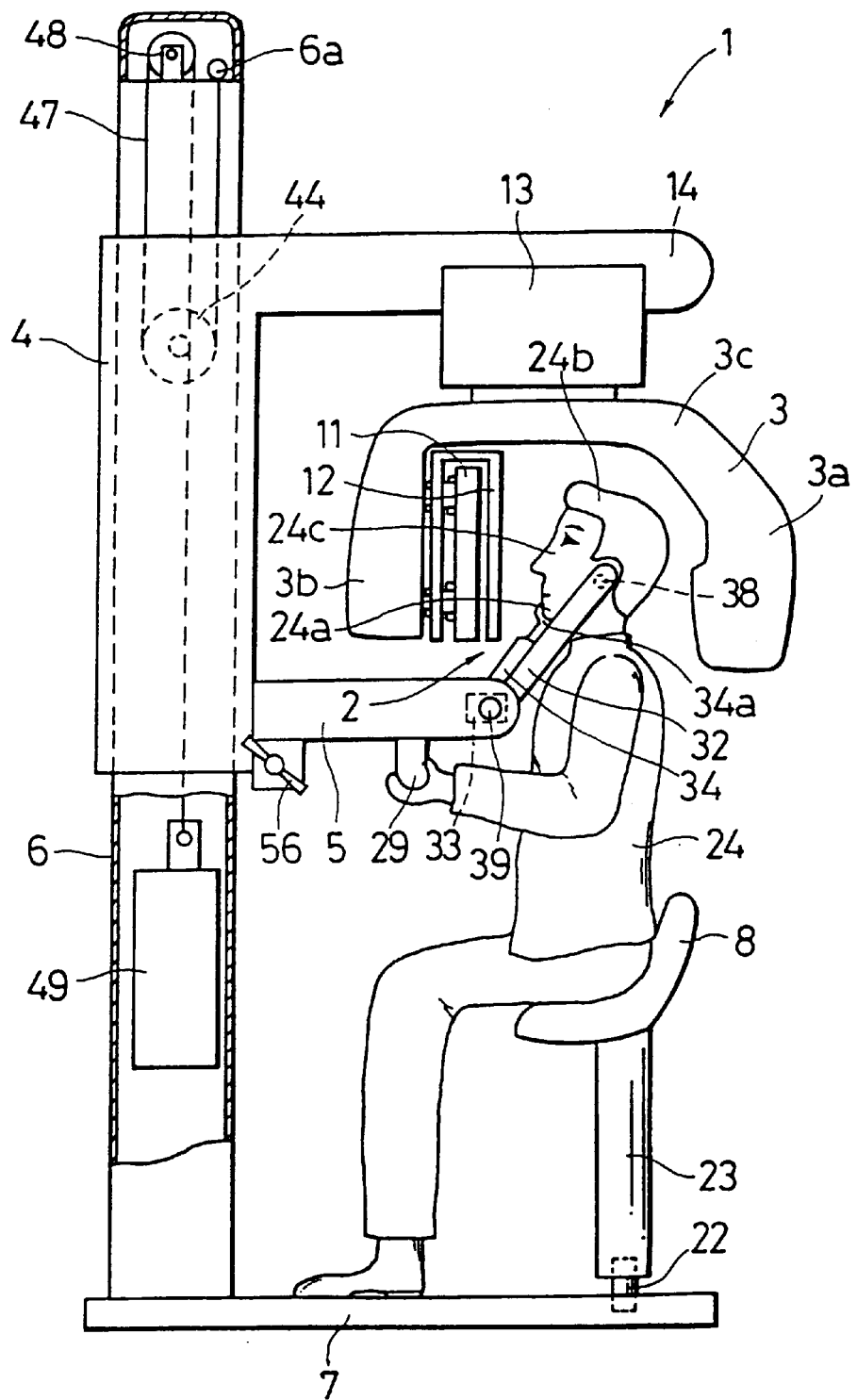
FIG. 2 is a partially cut-away side view for explaining the state of use of the radiographic apparatus 1.
Figure 3:
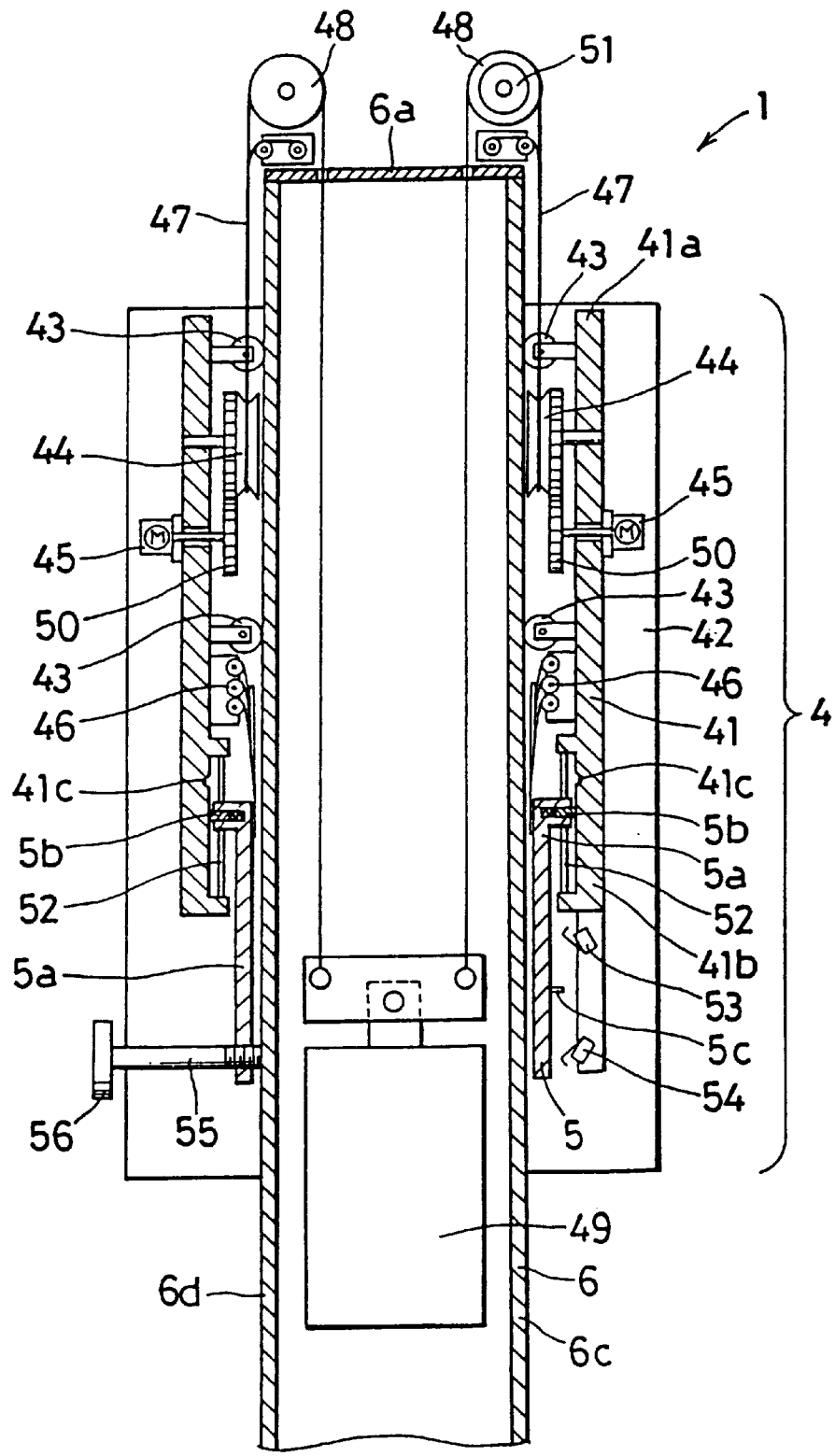
FIG. 3 is a sectional view of line 3—3 taken along FIG. 1.

FIG. 1 is a perspective view of a radiographic apparatus 1 in a first embodiment of the invention; FIG. 2 is a partially cut-away side view for explaining the state of use of the radiographic apparatus 1; and FIG. 3 is a sectional view as seen from section line 3—3 of FIG. 1. The radiographic apparatus 1 substantially comprises a head fixing device 2, a swivel arm 3, an ascending/descending main body 4, a patient frame 5, a post 6, a base 7, and a chair 8.

The head fixing device 2 is composed of a pair of right and left temporal holding members 31, 32 corresponding to both temporal sides of a patient 24, an opening mechanism 33 for moving the temporal holding members 31, 32 in mutually approaching and departing directions, a chin rest 34a, and guide means (not shown) of the chin rest 34a. By turning a dial 39, base ends 31a, 32a of the temporal holding members 31, 32 are moved in the mutually approaching or departing direction by the opening mechanism 33, and ear rods 37, 38 are attached to their free ends 31b, 32b. The temporal holding members 31, 32, and ear rods 37, 38 are made of materials high in X-ray permeability and rigidity, such as acrylic resin, carbon fiber reinforced plastics, and polycarbonate.

The swivel arm 3 is formed roughly in a U-form, and an X-ray generator and a slit plate are provided in one end 3a, while a film cassette 11 and a slit plate 12 are provided in the other end 3b, and also an X-ray sensor realized by displacement drive mechanism of film cassette 11 or CCD is incorporated therein.

The area in the middle 3c of the swivel arm 3 is suspended on a holding frame 14 through swivel means 13, and the holding frame is integrally extended from the ascending/descending main body 4. In the swivel means 13, a swivel mechanism for swiveling the swivel arm 3 and an XY table are incorporated. The swivel arm 3 can be moved along the contour of the dental arch of the patient, enabling to conduct curvature tomograph such as panoramic photograph, while plane tomography is also possible at an arbitrary section of teeth and a skull.

The ascending/descending main body 4 is movable on the post 6 in the vertical direction as described below. The ascending/descending main body 4 is provided with an elevatable patient frame 5 as mentioned later. On the top of the patient frame 5, an operation panel 27 realized by switch panel or the like for inputting radiographic conditions is provided, and a display device 28 realized by a liquid crystal display device or the like for displaying a support screen for input operation is provided adjacently thereto.

Furthermore, at the bottom of the patient frame 5, a handle 29 is provided, and by holding the handle 29, the patient 24 is stabilized in position during exposure, and also the shoulders of the patient 24 are not raised, so that the swivel arm 3 is not prevented from rotating The post 6 is set up from the base 7, and this base 7 is provided with an oscillating member 23 which is free to oscillate on a rotary shaft 22. The chair 8 is attached to the oscillating member 23, and the patient 24 is guided into a desired exposure position in the direction of arrow 25 by oscillation of the oscillating member 23 for taking a radiograph, so that the patient 24 can be guided smoothly without any feeling of fear or threat to the swivel arm 3 located near the head 34b.

The ascending/descending main body 4 roughly comprises, as shown in FIG. 3, a frame body 41, a case body 42, a pair of right and left guide wheels 43, moving pulleys 44, a motor 45, and a constant load spring 46. From its upper end 41a, the holding frame 14 is extended. On the surfaces confronting both sides 6c, 6d of the post 6 inside the frame body 41, guide wheels 43 for sliding both sides 6c, 6d are provided, so that the ascending/descending main body 4 is free to move up and down on the post 6.

The moving pulleys 44 are provided to confront both sides 6c, 6d in the inner circumference, and wires 47 having one end fixed to the top 6a of the post 6 are wound on the moving pulleys 44, and the other ends of the wires 47 are linked to balance weights 49 through fixed pulleys 48 provided at the top 6a, by way of the moving pulleys 44. The balance weights 49 are guided elevatably in the post 6. The moving pulleys 44 are engaged with gears 50 provided on the output shaft, and therefore owing to the rotational drive of the motor 45, the ascending/descending main body 4 can be moved up and down. When the ascending/descending main body reaches a desired position, rotation of the fixed pulleys 48 is blocked by an electromagnetic brake 51 provided in relation to one fixed pulley 48, so that the ascending/descending main body 4 may be stably held in a desired position.

At the lower end 41b of the frame body 41, a pair of right and left guide shafts 52 are set up parallel to the post 6, that is, parallel to the elevating direction of the ascending/descending main body 4. The guide shafts 52 are engaged with guide holes formed in a pair of guide pieces 5a of the patient frame 5, and the patient frame 5 is free to oscillate on the ascending/descending main body 4. At the upper ends of the guide pieces 5a, free ends of the constant load springs 46 having the base end side attached to the frame body 41 are connected. The number of constant load springs 46 is selected depending on the weight of the patient frame 5 to be suspended. Therefore, the operator can manually move the patient frame 5 with ease.

Locating protrusions 5b are provided in the guide pieces 5a, confronting the frame body 41 side, and the ascending/descending main body 4 is moved up or down in panoramic radiography so that the locating protrusions 5b may fit into locating recesses 41c. Moreover, an abutting piece 5c is formed in one guide piece 5a, and corresponding to this abutting piece 5c, a pair of upper and lower limit switches 53, 54 are provided in the frame body 41. The ascending/descending main body 4 is elevatable in the range of the limit switches 53, 54, relatively to the patient frame 5 as described below.

A stopper 55 is attached to the guide piece 5a of the patient frame 5, confronting the post 6, and a handle 56 is affixed to the stopper 55. The stopper 55 projects or retreats depending on the turning displacement of the handle 56, and contacts frictionally with the side 6d of the post 6 at the projecting position, and thus the patient frame 5 is positioned and fixed.

At the front side of the ascending/descending main body 4, a median line indication light beam generator 61, a plane section position indication light beam generator 62, and an oculoauricular horizontal line indication light beam generator 63 are provided so as to be opposite to the patient 24, while a curvature section position indication light beam generator 64 is provided at the other end 3b side of the swivel arm 3.

Figure 4:
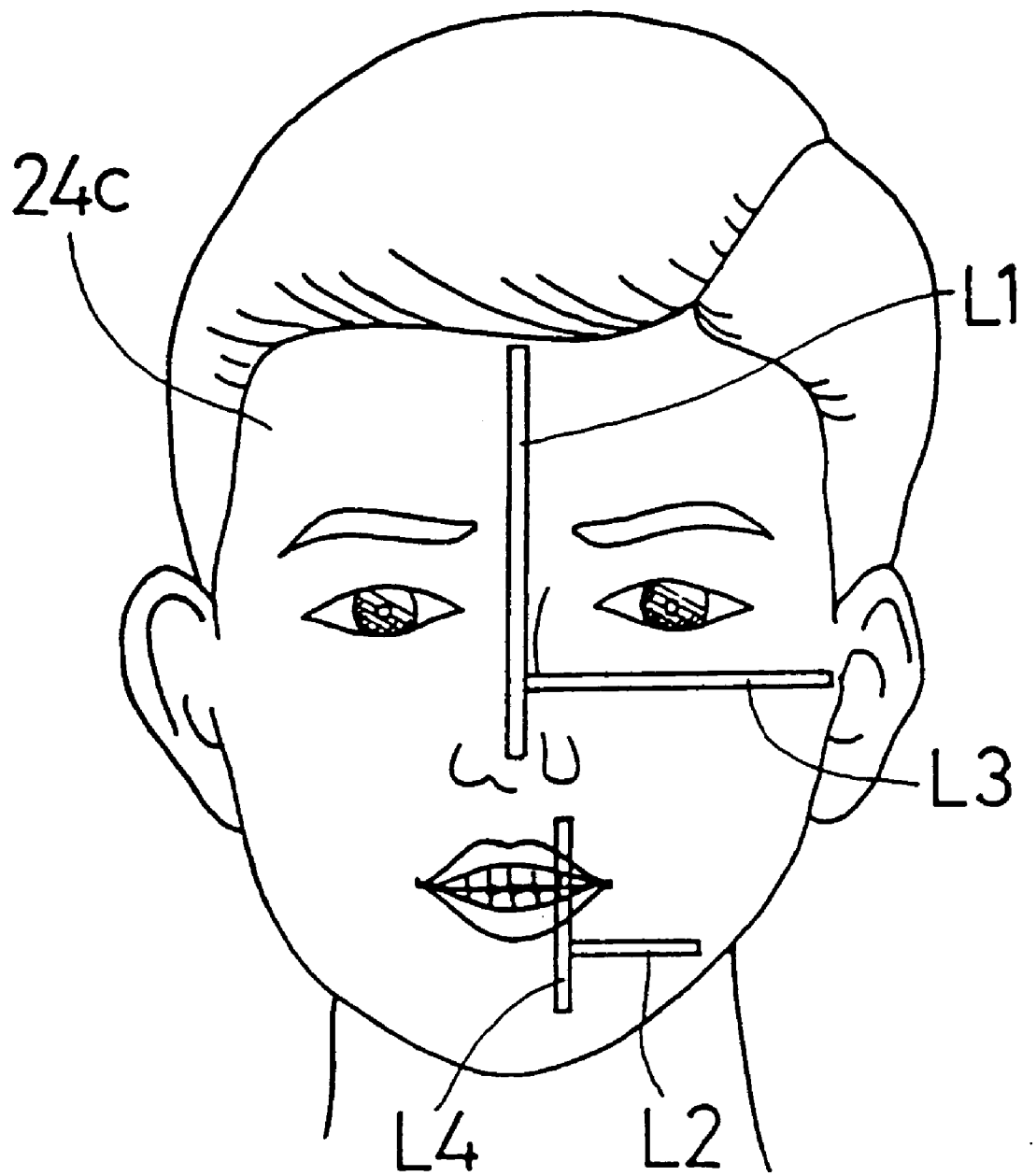
FIG. 4 is a diagram for explaining the positioning procedures of an ascending/descending main body 4.

In a thus constituted radiographic apparatus 1, when starting radiography, the operator first has the patient 24 sit on the chair 8, and rotates the oscillating member 23 in the direction of arrow 25 to guide the patient into a specified exposure position. Consequently, by referring to the median line beam emitted from the median line indication light beam generator 61 to the face 24c of the patient 24 as indicated by reference numeral L1 in FIG. 4, the patient frame 5 is lowered or raised by loosening the handle 56, and the projecting amount of the head fixing device 2 from the patient frame 5 is adjusted, and it is adjusted so that the ear rods 37, 38 may coincide with the external acoustic meatus of the patient 24. When the positioning the patient frame 5 is thus completed, the handle 56 is tightened, and the patient frame 5 is fixed to the post 6, and the dial 39 is rotated to move the temporal holding members 31, 32 so as to pinch the temporal sides of the patient 24, and the ear rods 37, 38 are fitted into the external acoustic meatus. At the same time, the chin rest support member 34 is expanded or contracted so that the jaw 24a of the patient 24 may be placed on the chin rest 34a.

When the adjustment corresponding to the height and other conditions of the patient 24 is completed, by referring to the indication light beam showing the central position in the vertical direction emitted from the plane section position indication light beam generator 62 as indicated by reference numeral L2, the motor 45 is driven until reaching a desired exposure position, and the ascending/descending main body 4 is moved up or down. Further, using the oculoauricular horizontal line indication beam indicated by reference numeral L3 emitted from the oculoauricular horizontal line indication light beam generator 63, the base end side of the chin rest support member 34 is oscillated and displaced as being guided by the guide means on the arcuate locus centered on the ear rods 37, 38, so that the eyes and external acoustic meatus may be matched on the indication light beam.

Thus plane tomography is enabled. In the case of curvature tomography, the swivel arm 3 is positioned by further referring to the indication light beam as indicated by reference numeral L4 from the curvature section position indication light beam generator 64.

Figure 5A:
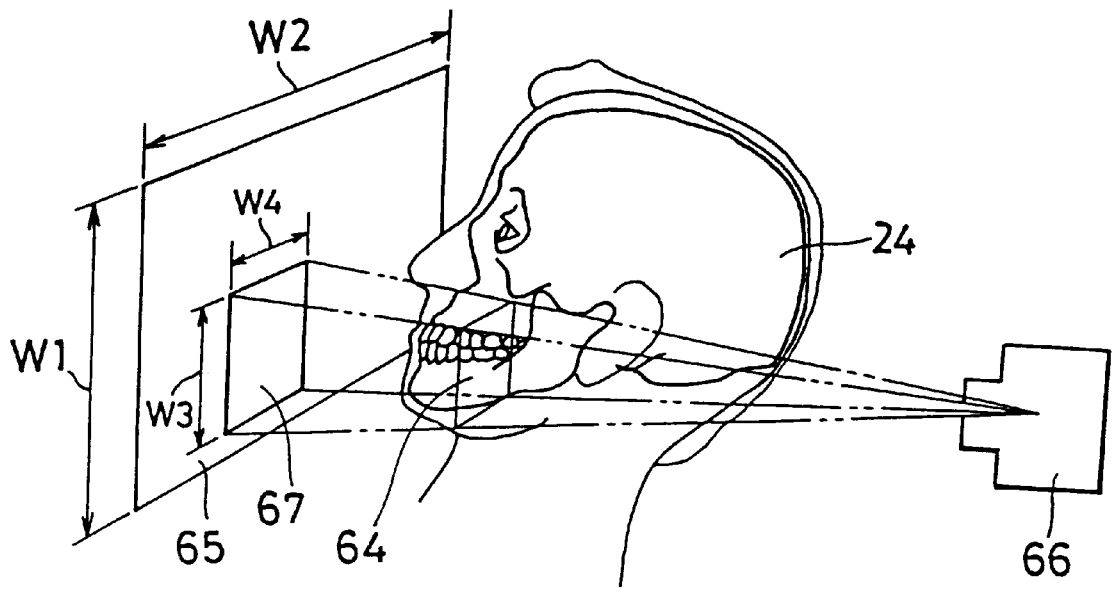
FIG. 5A and FIG. 5B are diagrams for explaining examples of the plane tomographic method.
Figure 5B:
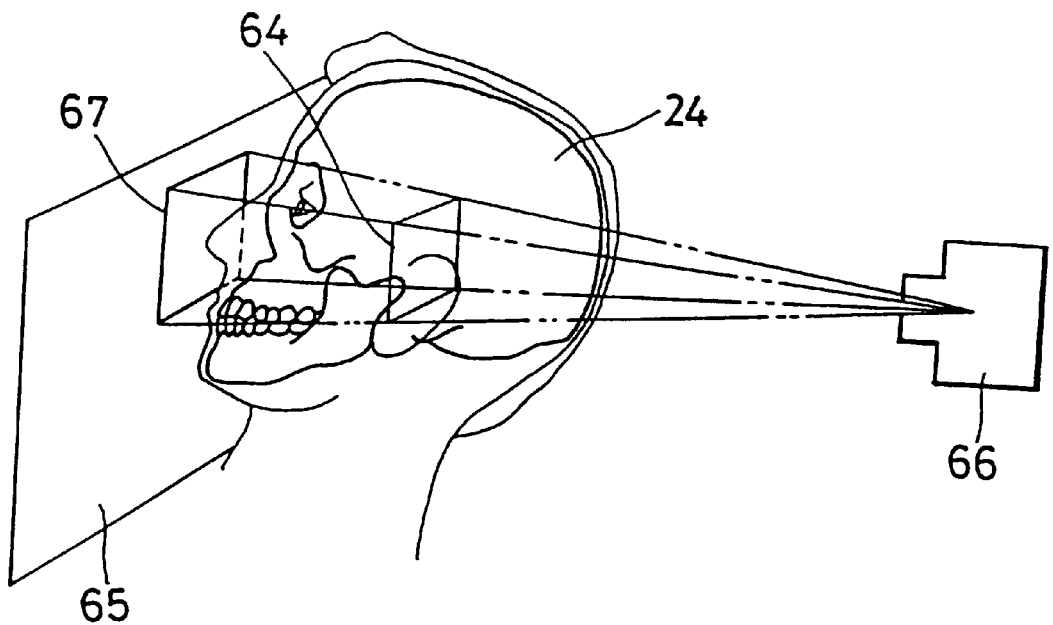

FIG. 5A and FIG. 5B are diagrams for explaining examples of plane tomography. Reference numeral 64 indicates the section plane to be taken, and therefore FIG. 5A shows the case of taking the submandibular anterior portion, and FIG. 5B shows the case of taking the mandibular joint area. A film 65 used in radiography placed in the film cassette 11 has a width W1 and a length W2, for example, 150 mm and 300 mm, respectively. In panoramic radiography, therefore, the primary slit disposed before the X-ray generator 66, and the secondary slit disposed immediately before the film 65 have a width nearly corresponding to the width W1. On the other hand, it is desired to make use of the film 65 effectively by suppressing the irradiation dose. In the prior art, however, since the patient frame 5 and swivel arm 3 could not be moved up and down relatively, in order to obtain a desired irradiation field 67, for example, 80 mm in width W3 and 70 mm in length W4, both the primary slit and secondary slit are narrowed in width.

By such a change in slit plate alone, however, the angle of the irradiation line to the horizontal plane may be inclined depending on the exposure position. In the invention, the ascending/descending main body 4 for supporting the swivel arm 3, and the patient frame 5 can be relatively displaced, so that such problem can be solved.

Figure 6:
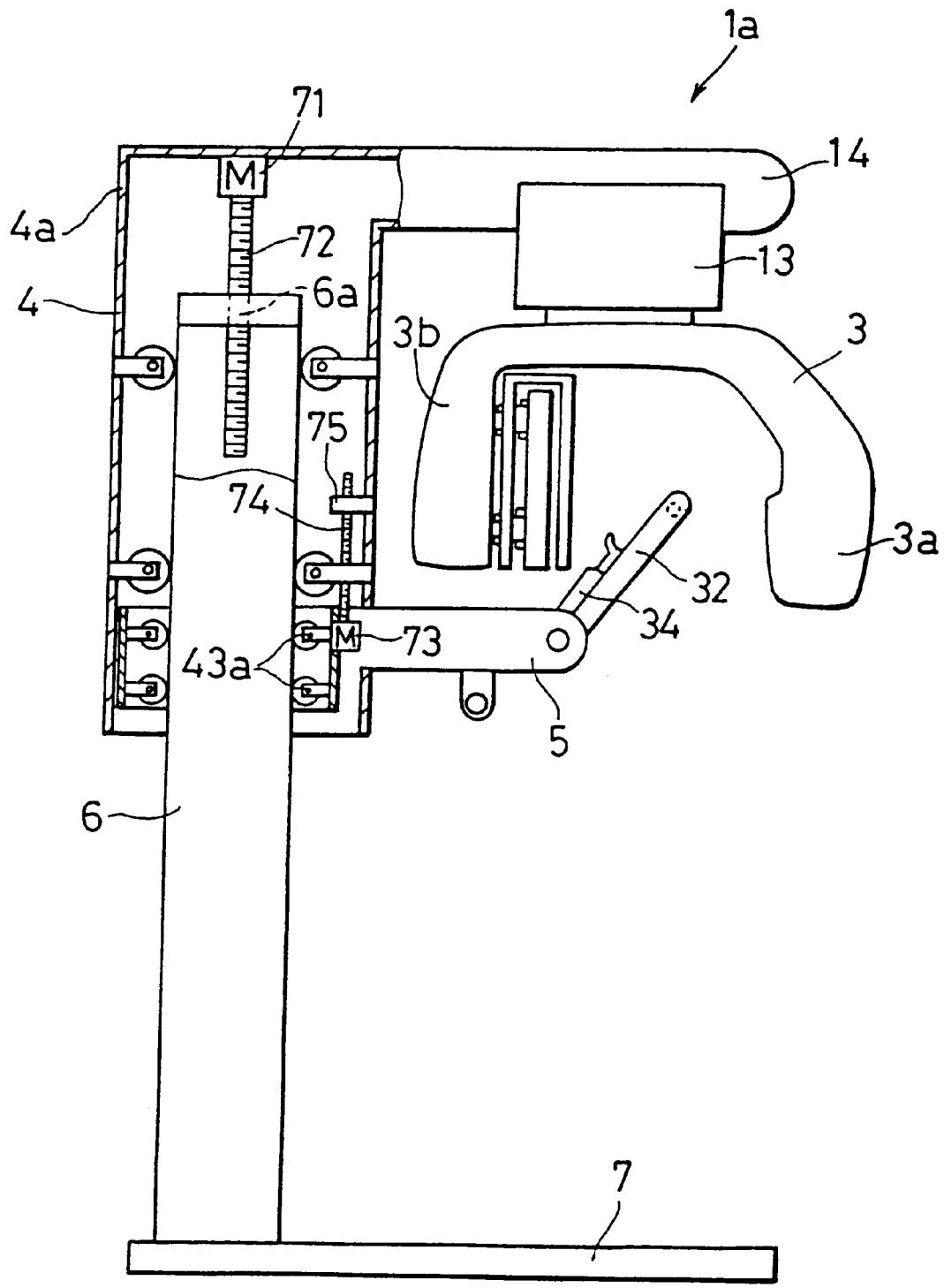
FIG. 6 is a partially cut-away side view of a radiographic apparatus 1a in a second embodiment of the invention.

FIG. 6 is a partially cut-away side view showing a radiographic apparatus 1a in a second embodiment of the invention, and this embodiment is similar to the preceding embodiment, and same reference numerals are attached to the corresponding parts. In this embodiment, it is of note that a motor 71 for ascending and descending is provided on the top 4a of the ascending/descending main body 4, and by rotating and driving this motor 71, a screw shaft 72 coupled to the output shaft of the motor 71 is rotated, and hence the ascending/descending main body 4 may be moved up and down on the top 6a of the post 6.

The patient frame 5 is provided with a guide wheel 43 so as to travel directly on a post 65. The patient frame 5 is further provided with a motor 73, and a screw shaft 74 coupled to the output shaft of the motor 73 is engaged with the screw hole of a holder 75 attached to the ascending/descending main body 4. Therefore, by rotating and driving the motor 73, the patient frame 5 and ascending/descending main body 4 may be relatively moved up and down.

In a thus constituted radiographic apparatus 1a, first the motor 71 is driven so that the patient frame 5 may be set to a desired height depending on the standing height and sitting height of the patient, then the motor 71 is driven depending on the exposure position, and the motor 73 is driven so that the patient frame 5 may be displaced in the opposite direction of the displacement direction of the lift main body in cooperation therewith, and the patient frame 5 rests on the post 6, so that only the height of the swivel arm 3 can be adjusted.

In this constitution, the ascending/descending main body 4 is provided with the motor 71 for lifting and lowering the patient frame 5 and ascending/descending main body 4, and the patient frame 5 is provided with the motor 73 for lifting and lowering the patient frame 5, but the ascending/descending main body 4 and patient frame 5 may displaced only relatively, and therefore, the patient frame 5 may be provided with the motor for the ascending/descending main body 4 and patient frame 5, and the ascending/descending main body 4 may be provided with a motor for the patient frame 5. The lifting mechanisms of the motors 71, 73 and screw shafts 72, 74 may be combinations of motor and wire, chain or belt the same as in the first embodiment shown in FIG. 1 through FIG. 3, or combinations of rack and pinion, or a known slide mechanism may be used instead of the guide wheels 43, 43a.

Figure 7:
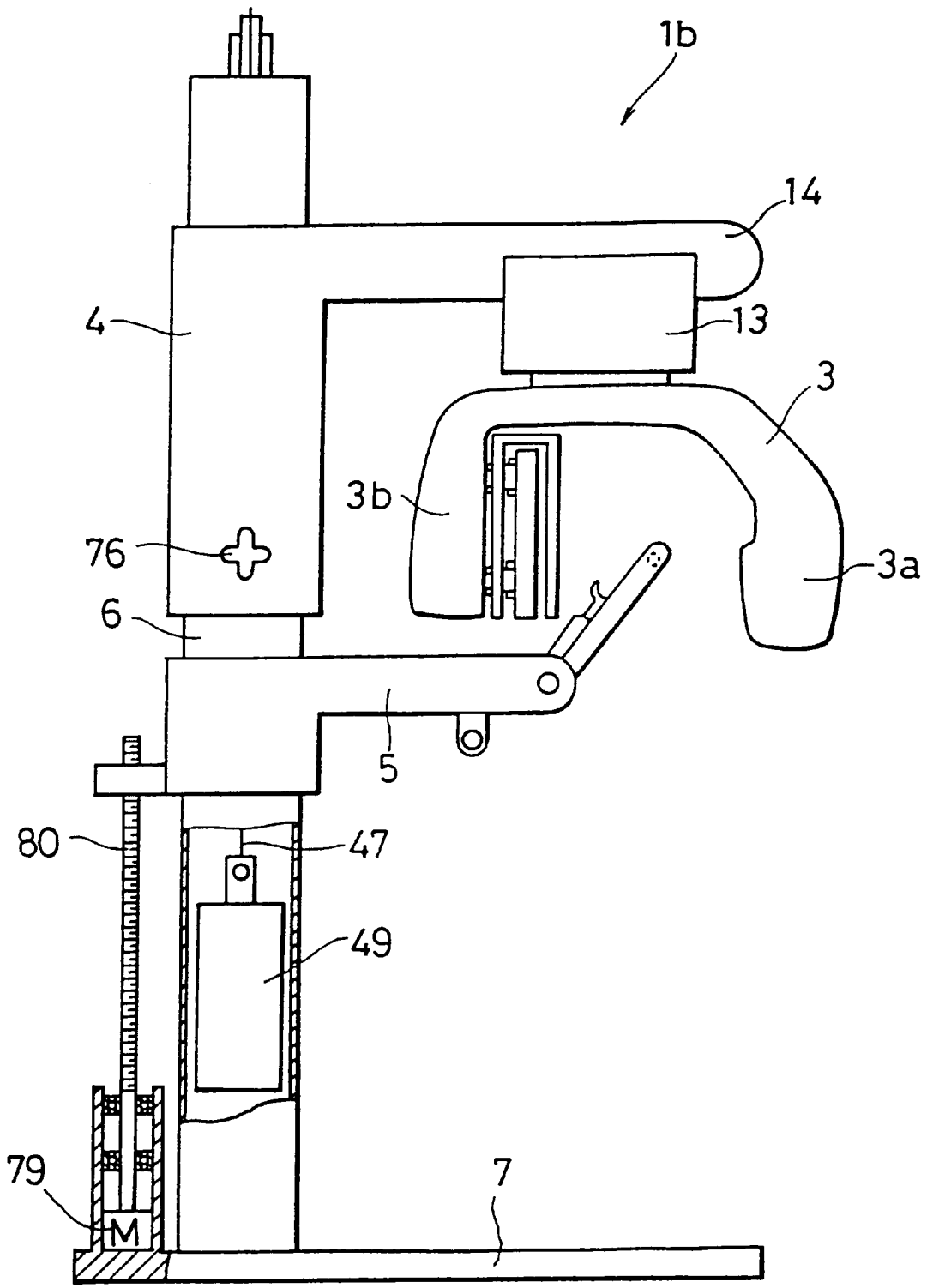
FIG. 7 is a partially cut-away side view of a radiographic apparatus 1b in a third embodiment of the invention.

FIG. 7 is a partially cut-away side view of a radiographic apparatus 1b in a third embodiment of the invention, and the same reference numerals are attached to the corresponding parts in the foregoing embodiments. What is of note in this embodiment is that the ascending/descending main body 4 is supported on the post 6 so as to be free to ascend and descend manually by using the balance weight 49 and wire 47 as shown in the first embodiment, and is held and fixed at that position by rotating a handle 76. The patient frame 5 is motor-driven to ascend and descend freely by means of a motor 79 installed on the base 7 and a screw shaft 80 coupled to its output shaft. In this way, the ascending/descending main body 4 and patient frame 5 are supported so as to be free to ascend and descend on the post 6 individually.

Figure 8:
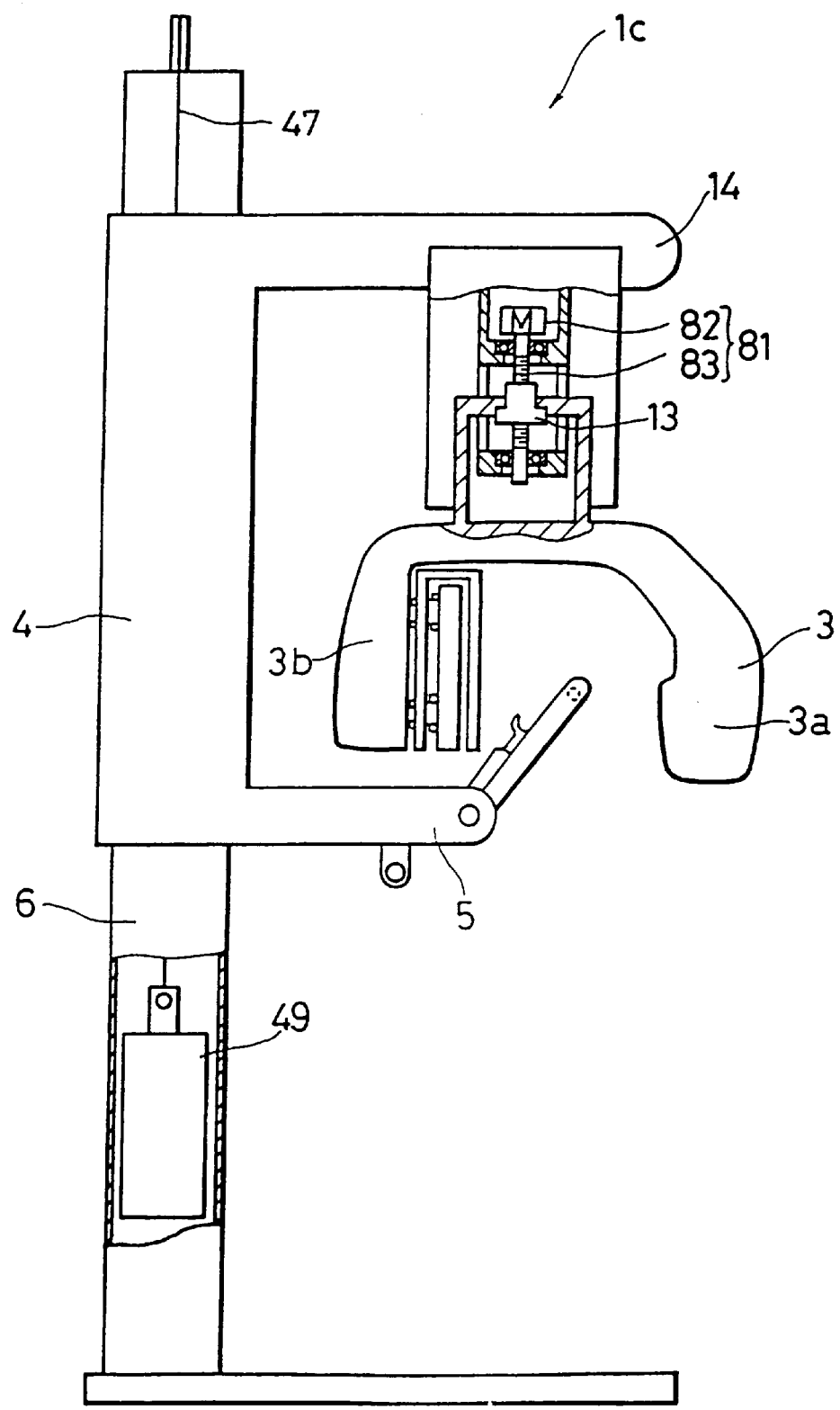
FIG. 8 is a partially cut-away side view of a radiographic apparatus 1c in a fourth embodiment of the invention.

FIG. 8 is a partially cut-away side view of a radiographic apparatus 1c in a fourth embodiment, and parts similar and corresponding to the embodiment in FIG. 7 are identified with the same reference numerals. In the embodiment, the ascending/descending main body 4 is elevatably supported manually on the post 6 by the balance weight 49 and wire 47, and the patient frame 5 is fixed integrally to the ascending/descending main body 4. Accordingly, a lift mechanism 81 is provided between the swivel means 13 and holding frame 14.

The lift mechanism 81 comprises a motor 82 and a screw shaft 83, and by rotating the motor 82 which is mounted on the holding frame 14 side, the swivel means 13 engaged with the screw shaft 83 is moved up and down. Thus, the patient frame 5 and swivel arm 3 can be displaced relatively.

Figure 9:
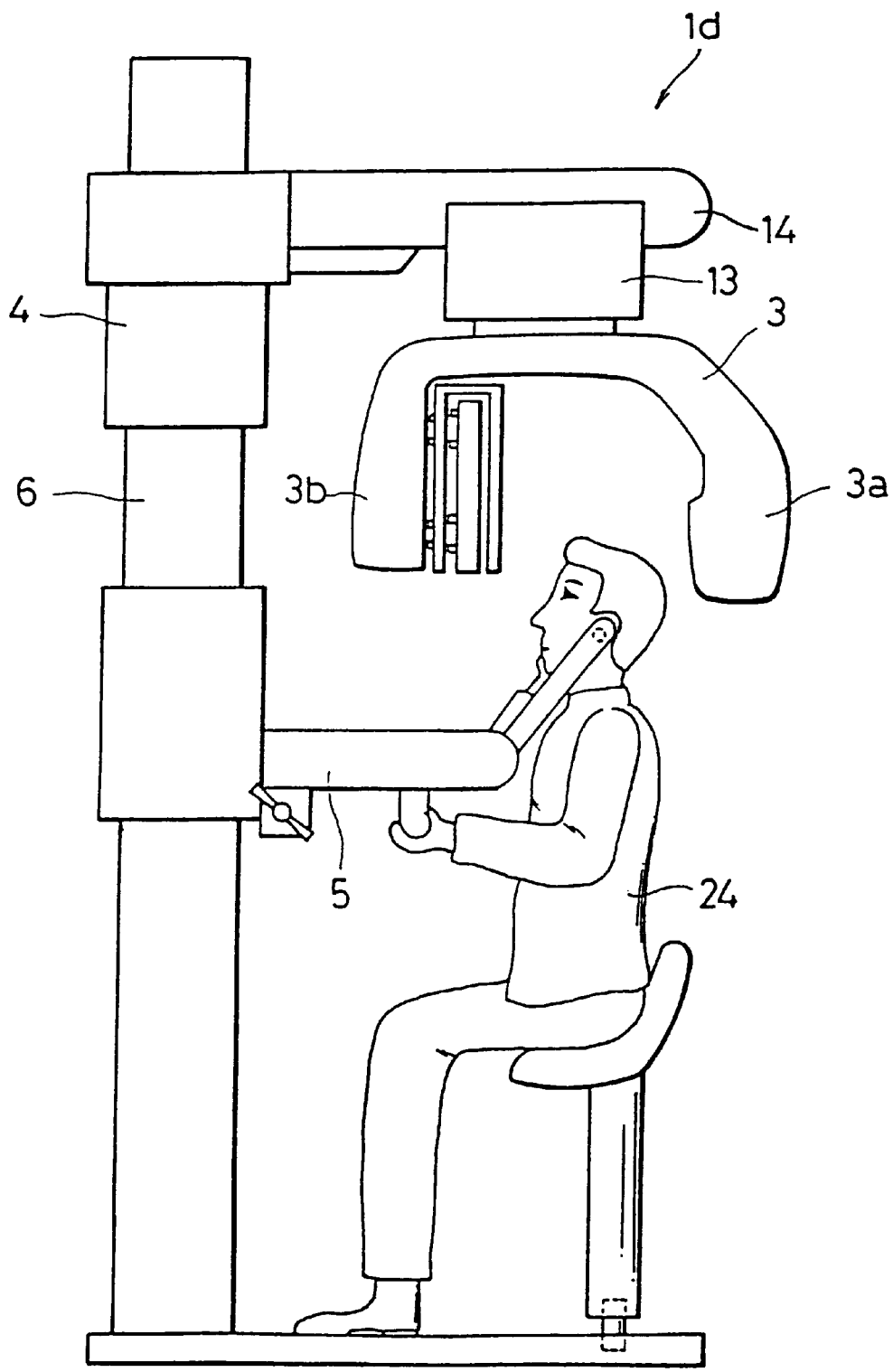
FIG. 9 is a partially cut-away side view of a radiographic apparatus 1d in a fifth embodiment of the invention.

FIG. 9 is a partially cut-away side view of a radiographic apparatus 1d in a fifth embodiment of the invention, and the same reference numbers are attached to the corresponding parts in the foregoing embodiments. In this embodiment, when the patient 24 is seated, the swivel arm 3 is moved sufficiently upward, and the feeling of fear and threat given to the patient 24 when leaving it can be further reduced. Such structure may be also employed in the foregoing radiographic apparatuses 1, 1a, 1b, and 1c.

Figure 10:
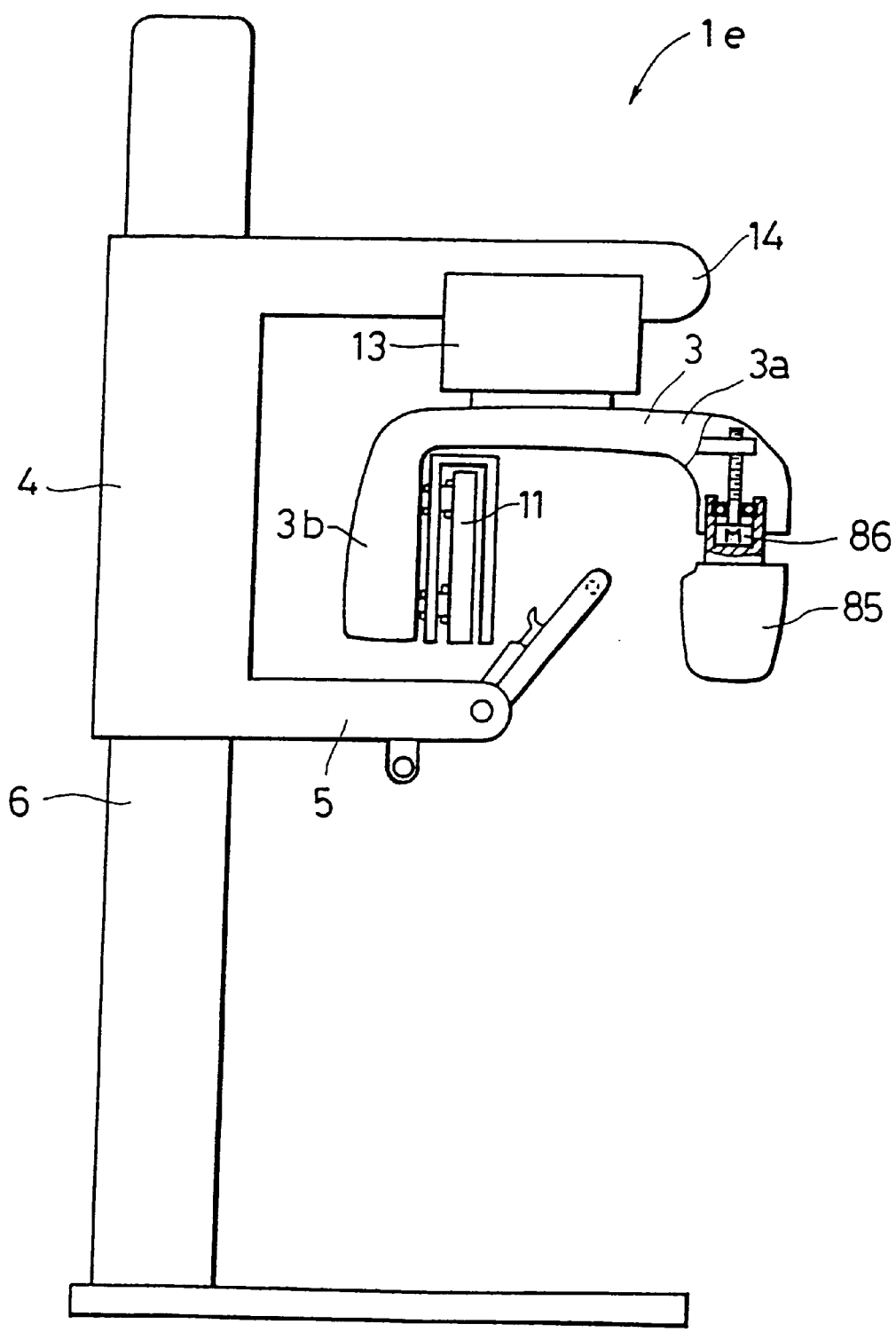
FIG. 10 is a partially cut-away side view of a radiographic apparatus 1e in a sixth embodiment of the invention.

FIG. 10 is a partially cut-away side view of a radiographic apparatus 1e in a sixth embodiment, and parts similar and corresponding to the embodiment in FIG. 8 are identified with same reference numerals. In the embodiment in FIG. 8, the swivel arm 3 is moved up and down by the swivel means 81, whereas in this embodiment, by contrast, only an X-ray generator 85 provided at one end 3a side of the swivel arm 3 is moved up and down by the lift means 86. Hence, a desired site can be taken in a simple constitution for relatively moving the X-ray generator 83 to the patient frame 5.

Figure 11:
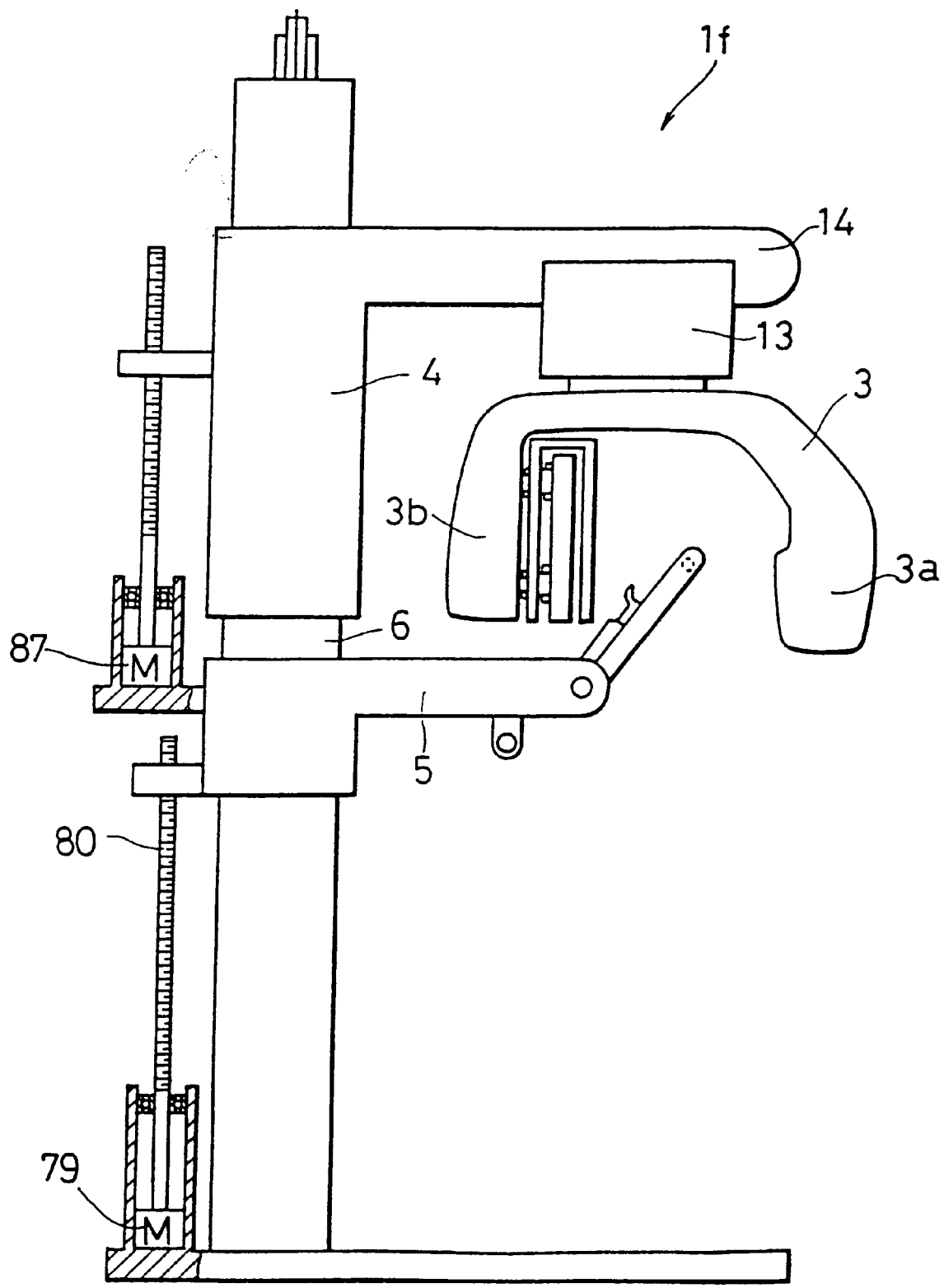
FIG. 11 is a partially cut-away side view of a radiographic apparatus 1f in a seventh embodiment of the invention.

FIG. 11 is a partially cut-away side view of a radiographic apparatus 1f in a seventh embodiment, and parts similar and corresponding to the embodiment in FIG. 7 are identified with the same reference numerals. In the embodiment, the patient frame 5 is moved up and down by a motor 79, and the ascending/descending main body 4 guided on the post 6 is moved up and down by a motor 87 attached to the patient frame 5. Thus, the patient frame 5 and swivel arm 3 can be elevated and lowered relatively.

Figure 12:
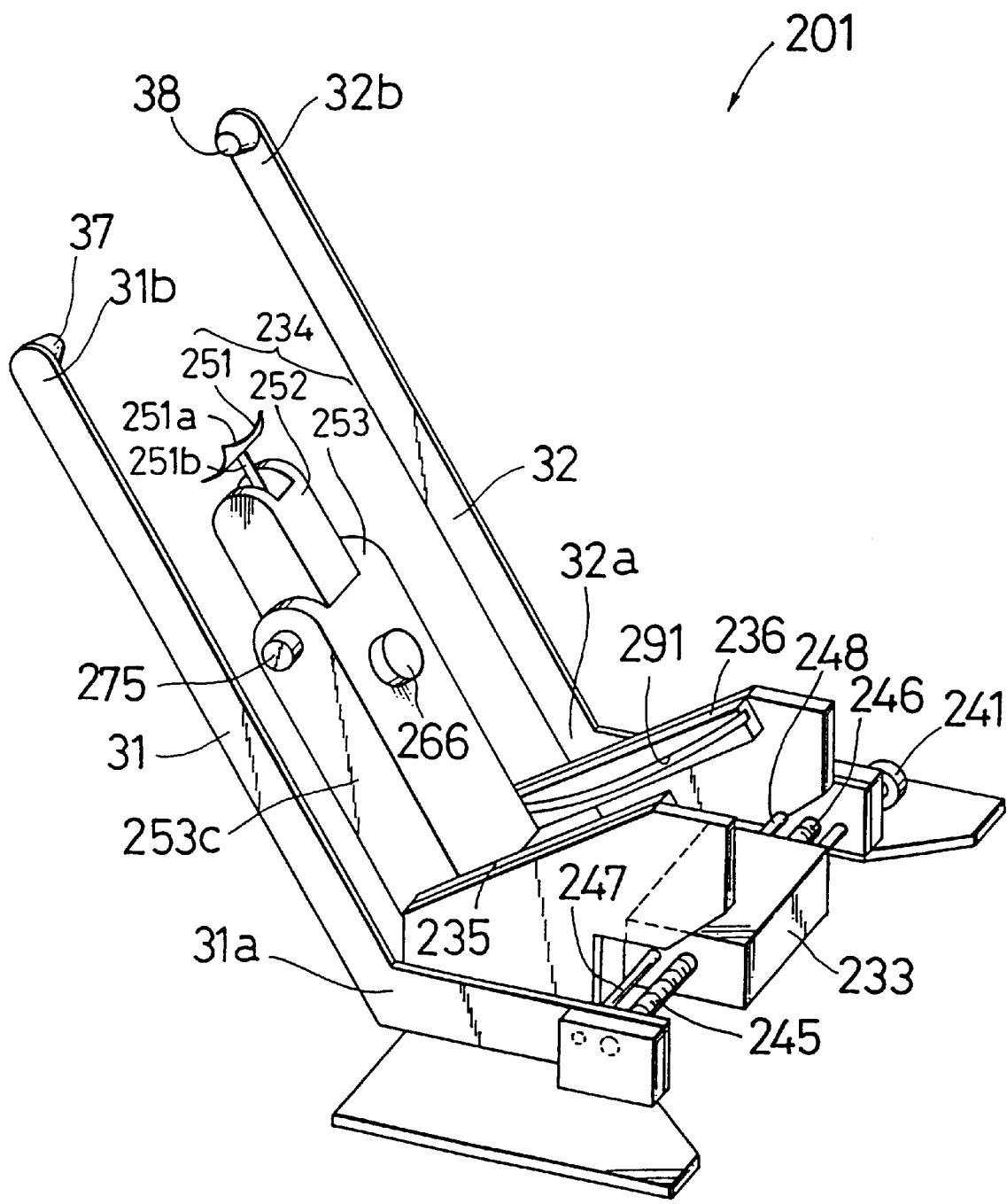
FIG. 12 is a perspective view of a head fixing device 201 used in a radiographic apparatus in an eighth embodiment of the invention.
Figure 13:
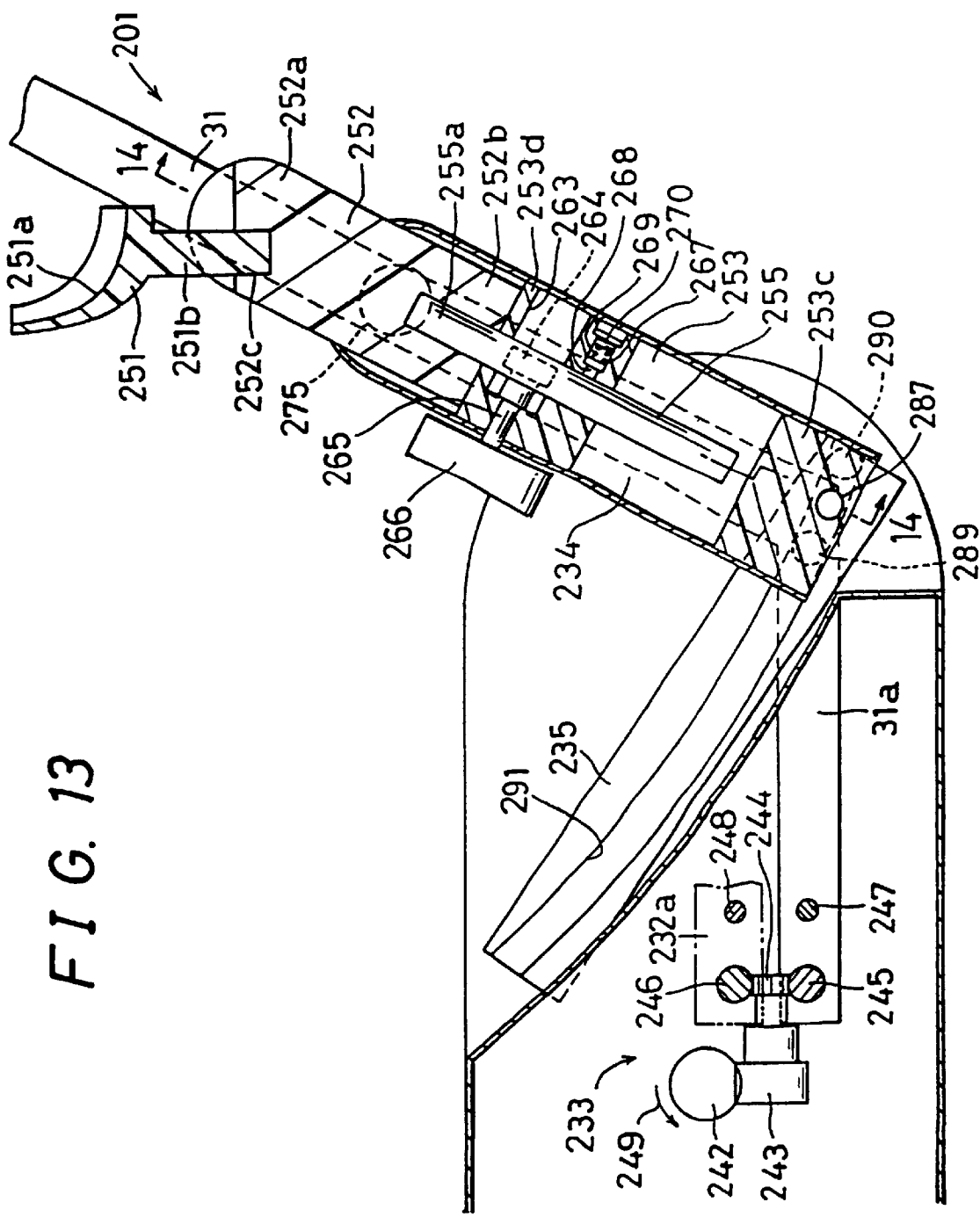
FIG. 13 is a longitudinal sectional view of the head fixing device 201 taken along the line 13—13 in FIG. 14.
Figure 14:
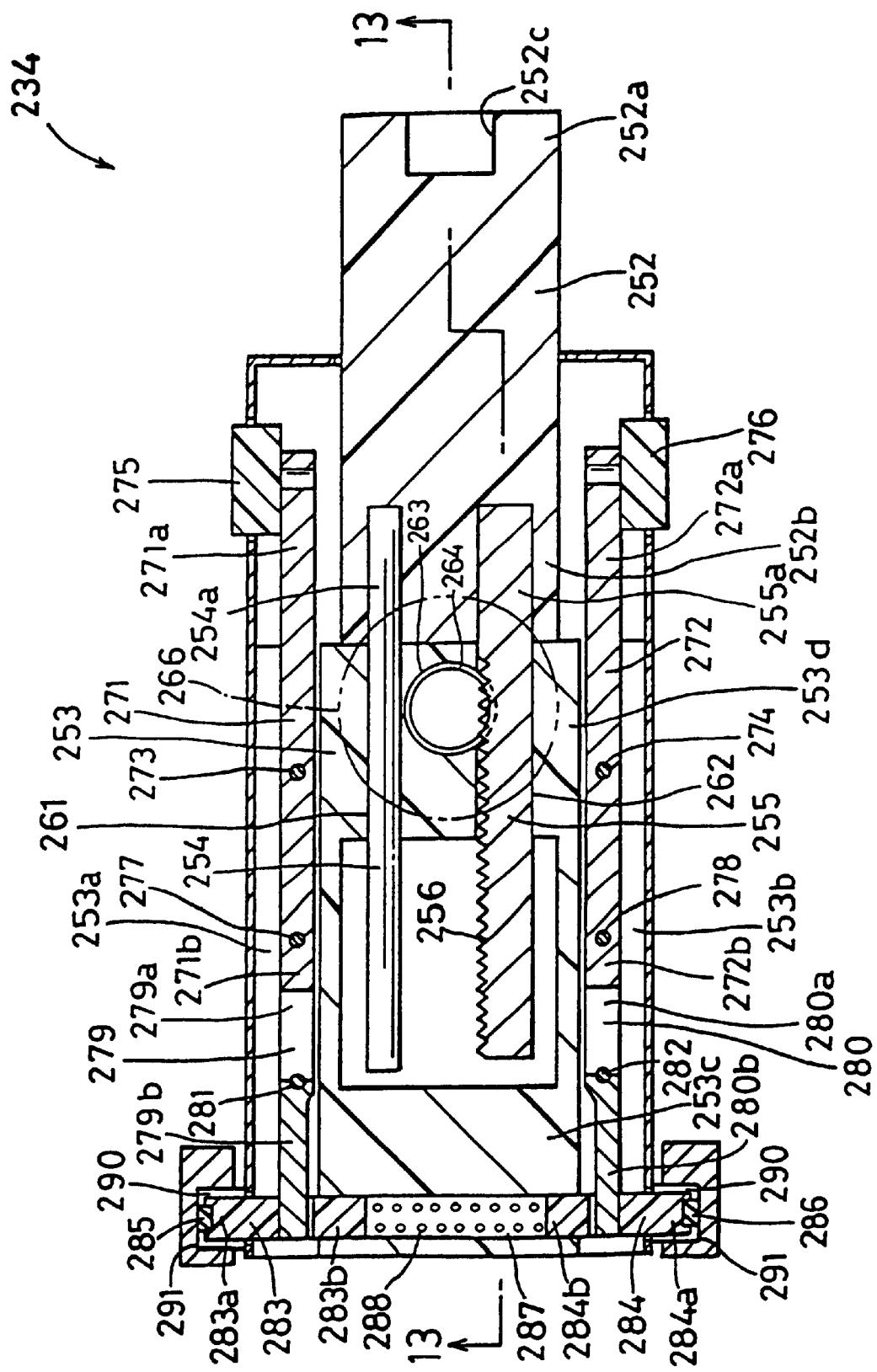
FIG. 14 is a sectional view taken along line 14—14 in FIG. 13.
Figure 15:
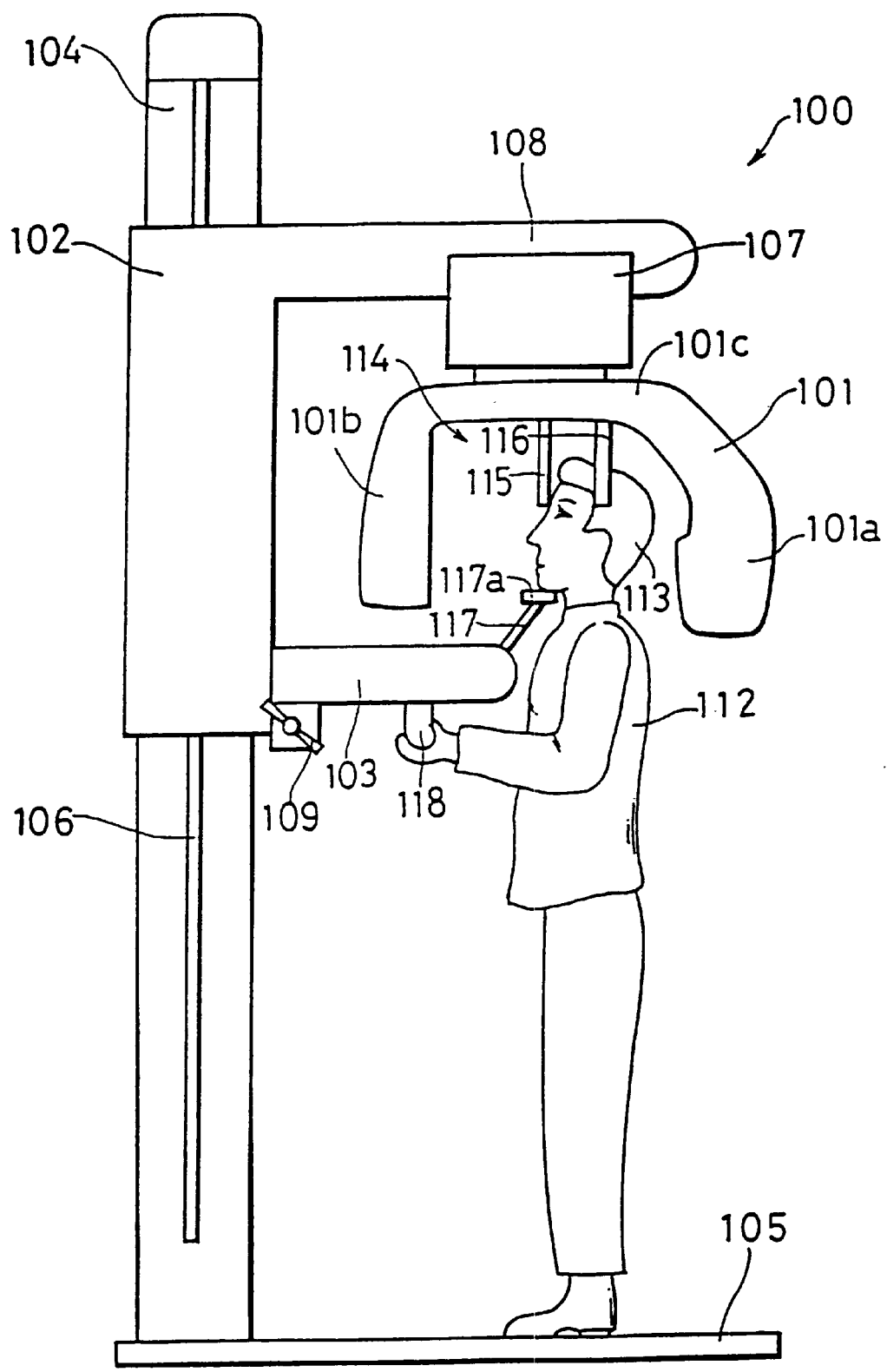
FIG. 15 is a sectional view of a conventional radiographic apparatus 100.
Figure 16:
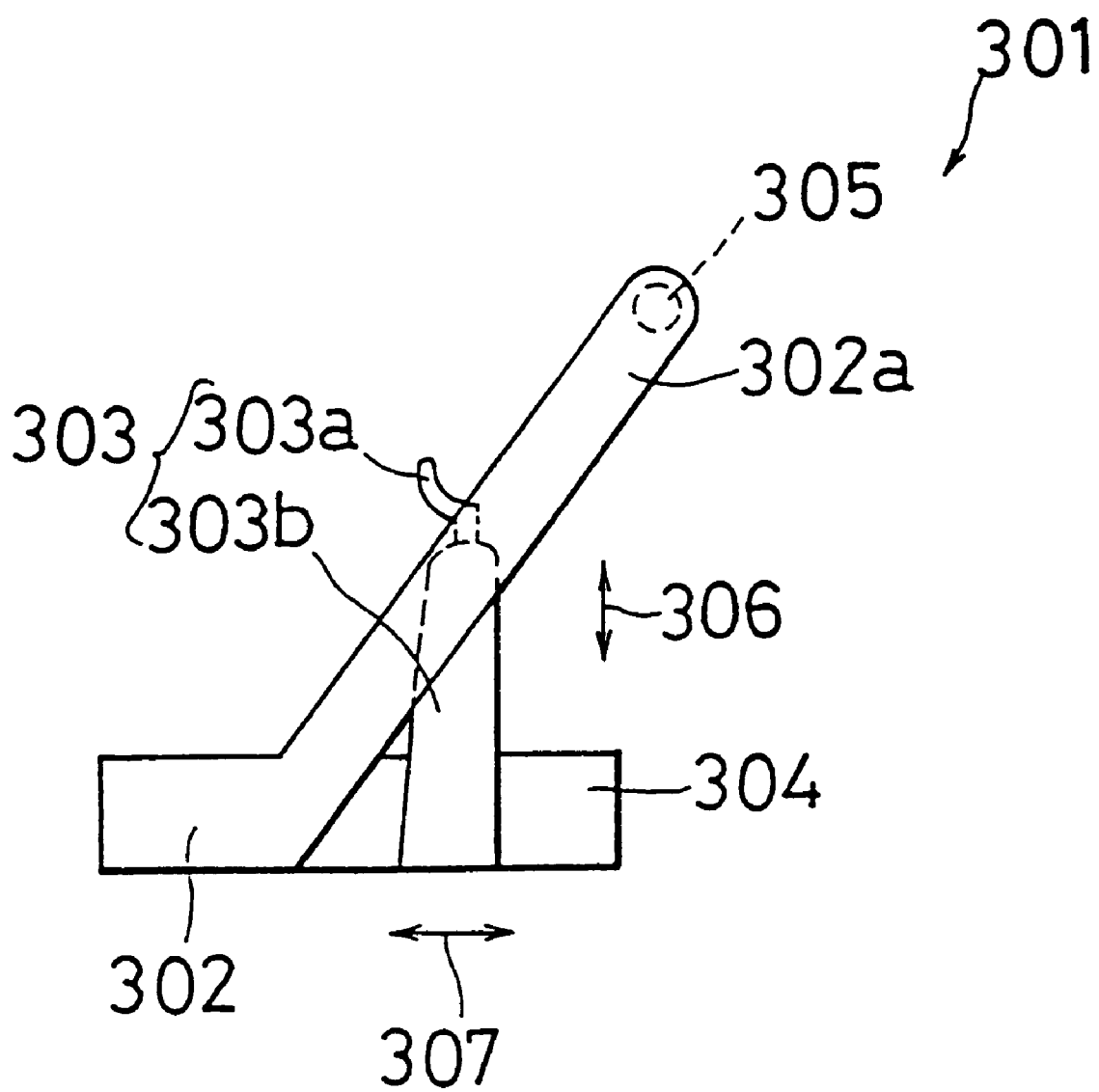
FIG. 16 is a sectional view schematically showing a conventional head fixing device 301.

FIG. 12 is a perspective view of a head fixing device 201 incorporated in the radiographic apparatus in an eighth embodiment of the invention. FIG. 13 is a partial longitudinal sectional view of the head fixing device 201, and FIG. 14 is a sectional view as seen from section line 14—14 in FIG. 13. FIG. 14 also shows a section line in FIG. 13 as 13—13 for reference. In the head fixing apparatus 201 of the embodiment, the same reference numerals are attached to parts corresponding and similar to the head fixing device 2 installed in the radiographic apparatus 1 in FIG. 1 through FIG. 5.

The opening mechanism 33 comprises a helical gear 242 rotating in cooperation with the rotary displacement of a dial 241, a helical gear 243 of the same size to be engaged with the helical gear 242, a gear 244 of small diameter rotating in cooperation with the helical gear 243, and rack gears 245, 246 disposed at mutually symmetrical positions to the gear 244. The basal ends 31a, 32a of the temporal holding members 31, 32 are supported on guide shafts 247, 248 so as to be mutually approaching and departing, and the base ends 31a, 32a are affixed with the rack gears 245, 246. When the dial 241 is turned, for example, to rotate and drive the helical gear 242 in the direction of arrow 249, the temporal holding members 31, 32 are moved and driven in the mutually approaching direction.

A chin rest 234, which is a support member, substantially comprises a platform 251, a telescopic member 252, and a main body 253. The platform 251 is shaped nearly in a T-form, having a recess 251a for mounting the jaw of the patient 24, and the T-form leg 251b is fitted and supported in a recess 252c formed at one end 252a of the telescopic member 252. From the other end 252b of the telescopic member 252, a guide shaft 254 and a drive shaft 255 having one ends 254a, 255a rested in the telescopic member 252 are extended to be parallel to each other. A rack gear 256 is formed on the guide shaft 254 side of the drive shaft 255.

At a free end 253d of the main body 253, there are formed a guide hole 261 for sliding the guide shaft 254, and an insertion hole 262 for inserting the drive shaft 255. Opposite to the insertion hole 262, a penetration hole 263 is formed vertically to the insertion hole 262, and a pinion tear 264 to be engaged with the rack gear 256 of the drive shaft 255 exposed in the penetration hole 263 is disposed in the penetration hole 263. The pinion gear 264 is connected to the dial 266 through a shaft 265. Therefore, by rotating the dial 266, the drive shaft 255 is let out or pulled in, and the telescopic member 252 is guided in the guide groove 254 and guide hole 261, so as to be driven telescopically.

A penetration hole 267 is pierced in the insertion hole 262, and from this penetration hole 267 and opposite to the drive shaft 244 of the insertion hole 262, brake means 268 realized by rubber or felt is confronted. The brake means 268 is thrust by a compression spring 269 provided in the penetration hole 267 in the direction of the drive shaft 255. The compression spring 269 also abuts against a piston 270, and by adjusting the projecting extent of the piston 270 into the penetration hole 267, the brake force of the brake means 268 on the drive shaft 244 can be regulated. For example, the telescopic member 252 can be expanded and contracted by rotation of the dial 266, and the brake force is set to such an extent that withdrawal of the telescopic member 252 may be prevented by the force of the patient 24 acting from the platform 251.

At both sides 253a, 253b of the main body 253, levers 271, 272 are oscillatably supported by pins 273, 274. At one-side ends 271a, 272a of the levers 271, 272, release buttons 275, 276 are provided. The other ends 271b, 272b of the levers 271, 272 are linked to one-side ends 279a, 280a of levers 279, 280. The levers 279, 280 are oscillatably supported by pins 281, 282, and the other ends 279b, 280b are linked to push pieces 283, 284. Thus, pairs of levers 271, 279; 272, 280 respectively compose link mechanisms.

At outer side ends 283a, 284a of the push pieces 283, 284, brake means 285, 286 made of materials of relatively large frictional force such as rubber and felt are provided. Inner side ends 283b, 284b of the push pieces 283, 284 are fitted into an insertion hole 287. At the inner side ends 283b, 284b, by a compression spring 288 provided in the insertion hole 287, a spring force is given in mutually departing directions, that is, in the outward protruding directions.

At the base end 253c of the main body 253, guide pins 289, 290 are set up on both sides 253a, 253b. The guide pins 289, 290 are fitted into the guide groove 291 formed in the guide means 235, 236, and thus the base end 253c of the main body 253 is supported so as to be oscillatable on the guide means 235, 236.

The brake means 285, 286 slide on the guide groove 291, and when the operator pushes in the release buttons 275, 276, resisting the elastic force of the compression spring 288, the brake means 285, 286 retreat into the main body 253, so that the chin rest 234 can be displaced on the guide means 235, 236.

On the other hand, the guide groove 291 is formed in an arc so that the distance to the ear rods 237, 238 may be always constant at any position. Therefore, when the radiologist pushes in the release buttons 275, 276 to displace the chin rest 234, the inclination angle of the patient 24 is changed around the external acoustic meatus, and at this time the distance from the jaw to any point on the guide groove 291 is constant, and therefore it is not necessary to adjust the telescopic stroke of the telescopic member 252 of the chin rest 234. Hence, the radiologist can fix the patient 24 in a desired position suited to radiography with excellent controllability.

Meanwhile, depending on the radiographic technique, instead of the temporal holding members 31, 32 having ear rods 37, 38, temporal holding members without ear rods 31, 32 may be used in exchange.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A medical radiographic apparatus including a post, a swivel arm, said swivel arm coupled to said post by a swivel means and a holding frame, an X-ray generator and an X-ray detector provided on opposite ends of said swivel arm and disposed to confront mutually with respect to the head of a patient whereby said X-ray generator and X-ray detector swivel about the head of the patient when the X-ray generator and X-ray detector are moved in synchronism in mutually parallel reverse directions, the apparatus comprising:

an ascending/descending main body from which the holding frame is extended, said main body being supported by the post so as to be free to move up and down, a patient support frame movably supported by said ascending/descending main body so as to be free to move up and down with respect to said ascending/descending main body, and a holding means comprising a pair of temporal holding members for supporting the patient upwardly extending from said patient support frame and a telescopic support member for supporting the patient provided between said temporal holding means and upwardly extending from said patient support frame.

* * * * *